US012075808B2

(12) United States Patent
Elli et al.

(10) Patent No.: US 12,075,808 B2
(45) Date of Patent: *Sep. 3, 2024

(54) PRODUCTION METHOD TO INCREASE BIOAVAILABILITY OF SUGARS FROM NATURAL COMPLEX POLYSACCHARIDES FOR HUMAN, ANIMAL AND AGRICULTURAL PURPOSES

(71) Applicant: COREE S.R.L., Milan (IT)

(72) Inventors: Marina Elli, Milan (IT); Chong-Yoon Lim, Milan (IT)

(73) Assignee: COREE S.R.L., Milan (IT)

( * ) Notice: Subject to any disclaimer, the term of this patent is extended or adjusted under 35 U.S.C. 154(b) by 0 days.

This patent is subject to a terminal disclaimer.

(21) Appl. No.: 17/601,316

(22) PCT Filed: Mar. 31, 2020

(86) PCT No.: PCT/EP2020/059126
§ 371 (c)(1),
(2) Date: Oct. 4, 2021

(87) PCT Pub. No.: WO2020/201284
PCT Pub. Date: Oct. 8, 2020

(65) Prior Publication Data
US 2022/0211082 A1    Jul. 7, 2022

(30) Foreign Application Priority Data

Apr. 3, 2019  (EP) .................................... 19167044

(51) Int. Cl.
| | |
|---|---|
| A23L 7/104 | (2016.01) |
| A23L 33/00 | (2016.01) |
| A23L 33/135 | (2016.01) |
| A61K 9/00 | (2006.01) |
| A61K 35/745 | (2015.01) |
| A61K 35/747 | (2015.01) |

(52) U.S. Cl.
CPC ............. *A23L 7/104* (2016.08); *A23L 33/135* (2016.08); *A23L 33/40* (2016.08); *A61K 9/0056* (2013.01); *A61K 35/745* (2013.01); *A61K 35/747* (2013.01); *A23V 2002/00* (2013.01); *A23V 2400/145* (2023.08); *A23V 2400/175* (2023.08); *A23V 2400/519* (2023.08)

(58) Field of Classification Search
CPC ........ A23L 7/104; A23L 33/135; A23L 33/40; A23L 33/21; A23L 2/382; A23L 19/00; A23L 23/00; A23L 25/40; A23L 29/065; A61K 9/0056; A61K 35/745; A61K 35/747; A61K 36/899; A61K 2236/00; A23V 2002/00; A23Y 2220/37; A23Y 2220/73; A23Y 2300/29

See application file for complete search history.

(56) References Cited

U.S. PATENT DOCUMENTS

| | | | |
|---|---|---|---|
| 2010/0098805 A1* | 4/2010 | Vykhodtsev | .......... A23L 33/135 |
| | | | 426/18 |
| 2017/0347689 A1 | 12/2017 | Wu et al. | |

FOREIGN PATENT DOCUMENTS

| | | | | |
|---|---|---|---|---|
| CN | 105146614 A | 12/2015 | | |
| CN | 108157973 A | 6/2018 | | |
| EP | 1169925 A1 * | 1/2002 | ........... | A23C 9/1234 |
| EP | 2848681 A1 | 3/2015 | | |
| JP | 2010-514428 A | 5/2010 | | |
| JP | 2012184261 A * | 9/2012 | | |
| KR | 10-2016-0063659 A | 6/2016 | | |
| WO | 2006039768 A1 | 4/2006 | | |
| WO | 2015/172191 A1 | 11/2015 | | |
| WO | WO-2017126959 A1 * | 7/2017 | ............. | A63L 29/00 |
| WO | WO-2017156548 A1 * | 9/2017 | ............. | A23K 10/18 |

OTHER PUBLICATIONS

Szajewska et al., Fermented infant formulas without live bacteria: a systematic review, Eur. J. Pediatr. 174:1413-1420, Published Sep. 11, 2015 (Year: 2015).*
Brumini et al., Whey proteins and their antimicrobial properties in donkey milk: a brief review, Dairy Sci. & Technol. 96:1-14, Published Jul. 23, 2015 (Year: 2015).*
Centers for Disease Control and Prevention Weaning Guide (Centers for Disease Control and Prevention, Nutrition, Weaning Guide, https://www.cdc.gov/nutrition/infantandtoddlernutrition/breastfeeding/weaning.html, page last reviewed Jul. 9, 2021) (Year: 2021).*
Tang et al. (Lactic acid fermentation from food waste with indigenous microbiota: Effects of pH, temperature and high OLR, Waste Management 52 (2016) 278-285), (Year: 2016).*
L. M. Lichtenberger, the Hydrophobic Barrier Properties of Gastrointestinal Mucus, Annual Review of Physiology, Mar. 1995, pp. 565-583, vol. 57.
Duary et al., Assessing the adhesion of putative indigenous probiotic lactobacilli to human colonic epithelial cells, The Indian Journal of Medical Research, Nov. 2011, pp. 664-671, vol. 134.
Deepika et al., Influence of fermentation conditions on the surface properties and adhesion of Lactobacillus rhamnosus GG, Microbial Cell Factories, Aug. 2012, vol. 11, Article No. 116.
Rousseaux et al. Lactobacillus acidophilus modulates intestinal pain and induces opioid and cannabinoid receptors, Nature Medicine, Jan. 2007, pp. 35-37, vol. 13, No. 1.
Wang et al., Activation of epidermal growth factor receptor mediates mucin production stimulated by p40, a Lactobacillus rhamnosus GG-derived protein, The Journal of Biological Chemistry, Jul. 2014, pp. 20234-20244, vol. 289, No. 29.

(Continued)

*Primary Examiner* — Louise W Humphrey
*Assistant Examiner* — Alexander M Duryee
(74) *Attorney, Agent, or Firm* — IP & T GROUP LLP

(57) ABSTRACT

A fermented food product or food supplement comprising a vegetable substrate fermented by a probiotic blend is disclosed. The fermented food product or food supplement according to the invention is useful in particular for improving natural maternity, lactation and baby weaning. The invention also discloses a process for the preparation of the fermented food product or food supplement comprising the fermentation of a vegetal substrate with the probiotic blend.

11 Claims, 1 Drawing Sheet

(56) References Cited

OTHER PUBLICATIONS

Wong et al., Pharmacogenetic trial of a cannabinoid agonist shows reduced fasting colonic motility in patients with honconstipated irritable bowel syndrome, Gastroenterology, Nov. 2011, pp. 1638-1647, vol. 141, Issue No. 5.
Hermanson et al., Cannabinoids, endocannabinoids, and cancer, Cancer and Metastasis Reviews, Oct. 2011, vol. 30, pp. 599-612.
Johansson et al., Administration of different Lactobacillus strains in fermented oatmeal soup: In vivo colonization of human intestinal mucosa and effect on the indigenous flora, Applied and Environmental Microbiology, Jan. 1993, vol. 59, No. 1, pp. 15-20.
El-Abasy et al., Mixes of Carrot Juice and Some Fermented Dairy Products: Potentiality as Novel Functional Beverages, Food and Nutrition Sciences, Feb. 2012, pp. 233-239, vol. 3, No. 2.
Daneluti et al., Study of thermal behavior of phytic acid, Brazilian Journal of Pharmaceutical Sciences, Jun. 2013, pp. 275-283, vol. 49, No. 2.
Marshall et al., Traditional Fermented Foods and Beverages for Improved Livelihoods, FAO Diversification booklet No. 21, Jan. 2011, ISBN: 1810-0775.
Deshpande et al., Fermented Grain Legumes, Seeds and Nuts: A Global Perspective, FAO Agricultural Services Bulletin No. 142, Chapter 1, Dec. 2000, ISBN: 9251044449.
Deshpande et al., Fermented Grain Legumes, Seeds and Nuts: A Global Perspective, FAO Agricultural Services Bulletin No. 142, Chapter 2 and 3, Dec. 2000, ISBN: 9251044449.
Haard et al., Fermented Cereals: A Global Perspective, FAO Agricultural Services Bulletin No. 138, Dec. 1999, ISBN: 9251042969.
Battcock et al., Fermented Fruits and Vegetables: A Global Perspective, FAO Agricultural Services Bulletin No. 134, Dec. 1998, ISBN: 9251042268.
Selhub et al., Fermented foods, microbiota, and mental health: ancient practice meets nutritional psychiatry, Journal of Physiological Anthropology, Jan. 2014, vol. 33, No. 2.
Tamang et al., Review: Diversity of Microorganisms in Global Fermented Foods and Beverages, Frontiers in Microbiology, Mar. 2016, vol. 7, No. 377.
Araya et al., Probiotics in food Health and nutritional properties and guidelines for evaluation, FAO food and nutrition paper No. 85, Jun. 2006, ISSN: 0254-4725.
Scholtens et al., Bifidogenic Effects of Solid Weaning Foods With Added Prebiotic Oligosaccharides: A Randomised Controlled Clinical Trial, Journal of Pediatric Gastroenterology and Nutrition, vol. 42, No. 5, May 2006, pp. 553-559.
Maria E. Barbian et al., To Start or Not: Factors to Consider when Implementing Routine Probiotic Use in the NICU, Early Human Development, vol. 135, Jun. 10, 2019, pp. 66-71, Elsevier, Netherlands.
Asma Kazemi et al., Effect of probiotic and synbiotic supplementation on inflammatory markers in health and disease status: A systematic review and meta-analysis of clinical trials, Clinical Nutrition, vol. 39, No. 3, Apr. 17, 2019, pp. 789-819, Elsevier, Netherlands.
Probiotical, Our Probiotic Strains, Jan. 1, 2016, Probiotical S.P.A., Italy.
Luis Fontana et al., Sources, isolation, characterisation and evaluation of probiotics, British Journal of Nutrition, vol. 109, No. S2, Jan. 1, 2013, pp. S35-S50, UK.
M. Popova et al., Beneficial effects of probiotics in upper respiratory tract infections and their mechanical actions to antagonize pathogens, Journal of Applied Microbiology, vol. 113, No. 6, Dec. 1, 2012, pp. 1305-1318, Wiley-Blackwell Publishing Ltd, GB.
James W. Dekker et al., Safety aspects of probiotic bacterial strains Lactobacillus rhamnosus HN001 and Bifidobacterium animalis subsp. *lactis* HNO19 in human infants aged 0-2 years, International Dairy Journal, vol. 19, 2009, pp. 149-154, Elsevier, Netherlands.
Joint FAO/WHO Working Group Report, Probiotics in food—Health and nutritional properties and guidelines for evaluation, FAO Food and Nutrition Paper 85, 2006, World Health Organization and Food and Agriculture Organization of the United Nations.
J. S. Zhou et al., Immunostimulatory probiotic Lactobacillus rhamnosus HN001 and Bifidobacterium lactis HN019 do not induce pathological inflammation in mouse model of experimental auto-immune thyroidites, International Journal of Food Microbiology, vol. 103, 2005, pp. 97-104, Elsevier, Netherlands.
J. S. Zhou et al., Potential probiotic lactic acid bacteria Lactobacillus rhamnosus (HN001), Lactobacillus acidophilus (HN017) and Bifidobacterium lactis (HN019) do not degrade gastric mucin in vitro, International Journal of Food Microbiology, vol. 63, 2001, pp. 81-90, Elsevier, Netherlands.
J. S. Zhou et al., Inability of Probiotic Bacterial Strains Lactobacillus rhamnosus HN001 and Bifidobacterium lactis HN019 to Induce Human Platelet Aggregation In Vitro, Journal of Food Protection, vol. 68, No. 11, 2005, pp. 2459-2464, Elsevier, Netherlands.
Maria E. Barbian et al., To Start or Not: Factors to Consider when Implementing Routine Probiotic Use in the NICU, Early Human Development, vol. 135, Jun. 10, 2019, pp. 66-71, XP085743265, ISSN: 0378-3782, Doi: 10.1016/J.EARLHUMDEV.2019.05.009.
Asma Kazemi et al., Effect of probiotic and synbiotic supplementation on inflammatory markers in health and disease status: A systematic review and meta-analysis of clinical trials, Clinical Nutrition, vol. 39, No. 3, Apr. 17, 2019, pp. 789-819, XP086055095, ISSN: 0261-5614, DOI: 10.1016/J.CLNU.2019.04.004.
Probiotical, Our Probiotic Strains, Jan. 1, 2016, Probiotical S.P.A., XP055382106, Retrieved from the Internet: URL:http://bart.pl/wp-content/uploads/2016/11 /ceppi_2016_OK.pdf.
Luis Fontana et al., Sources, isolation, characterisation and evaluation of probiotics, British Journal of Nutrition, vol. 109, No. S2, Jan. 1, 2013, pp. S35-S50, XP05530757 4, UK ISSN: 0007-1145, DOI: 10.1017/S0007114512004011.
M. Popova et al., Beneficial effects of probiotics in upper respiratory tract infections and their mechanical actions to antagonize pathogens, Journal of Applied Microbiology, Wiley-Blackwell Publishing Ltd, GB vol. 113, No. 6, Dec. 1, 2012, pp. 1305-1318, XP002711684, ISSN: 1364-5072, DOI: 10.1111 /J.1365-2672.2012.05394.X Retrieved from the Internet: URL:http://onlinelibrary.wiley.com/doi/10.1111 /.1365-2672.2012.05394.x/ abstract.
James W. Dekker et al., Safety aspects of probiotic bacterial strains Lactobacillus rhamnosus HN001 and Bifidobacterium animalis subsp. *lactis* HN019 in human infants aged 0-2 years, International Dairy Journal, vol. 19, 2009, pp. 149-154.
Joint FAO/WHO Working Group Report, Probiotics in food—Health and nutritional properties and guidelines for evaluation, FAO Food and Nutrition Paper 85, Oct. 1, 2001, World Health Organization and Food and Agriculture Organization of the United Nations.
J. S. Zhou et al., Immunostimulatory probiotic Lactobacillus rhamnosus HN001 and Bifidobacterium lactis HN019 do not induce pathological inflammation in mouse model of experimental auto-immune thyroidites, International Journal of Food Microbiology, vol. 103, 2005, pp. 97-104.
J. S. Zhou et al., Potential probiotic lactic acid bacteria Lactobacillus rhamnosus (HN001), Lactobacillus acidophilus (HN017) and Bifidobacterium lactis (HN019) do not degrade gastric mucin in vitro, International Journal of Food Microbiology, vol. 63, 2001, pp. 81-90.
J. S. Zhou et al., Inability of Probiotic Bacterial Strains Lactobacillus rhamnosus HN001 and Bifidobacterium lactis HN019 to Induce Human Platelet Aggregation In Vitro, Journal of Food Protection, vol. 68, No. 11, 2005, pp. 2459-2464.
Extended European Search Report for the European Patent Application No. 19208263.4 issued by the European Patent Office on Mar. 27, 2020.
International Search Report for the PCT Application No. PCT/EP2020/081683 by the European Patent Office on Nov. 1, 2021.
Office Action for Korean Patent Application No. 10-2021-7033293 issued by the Korean Patent Office on Mar. 22, 2024.

* cited by examiner

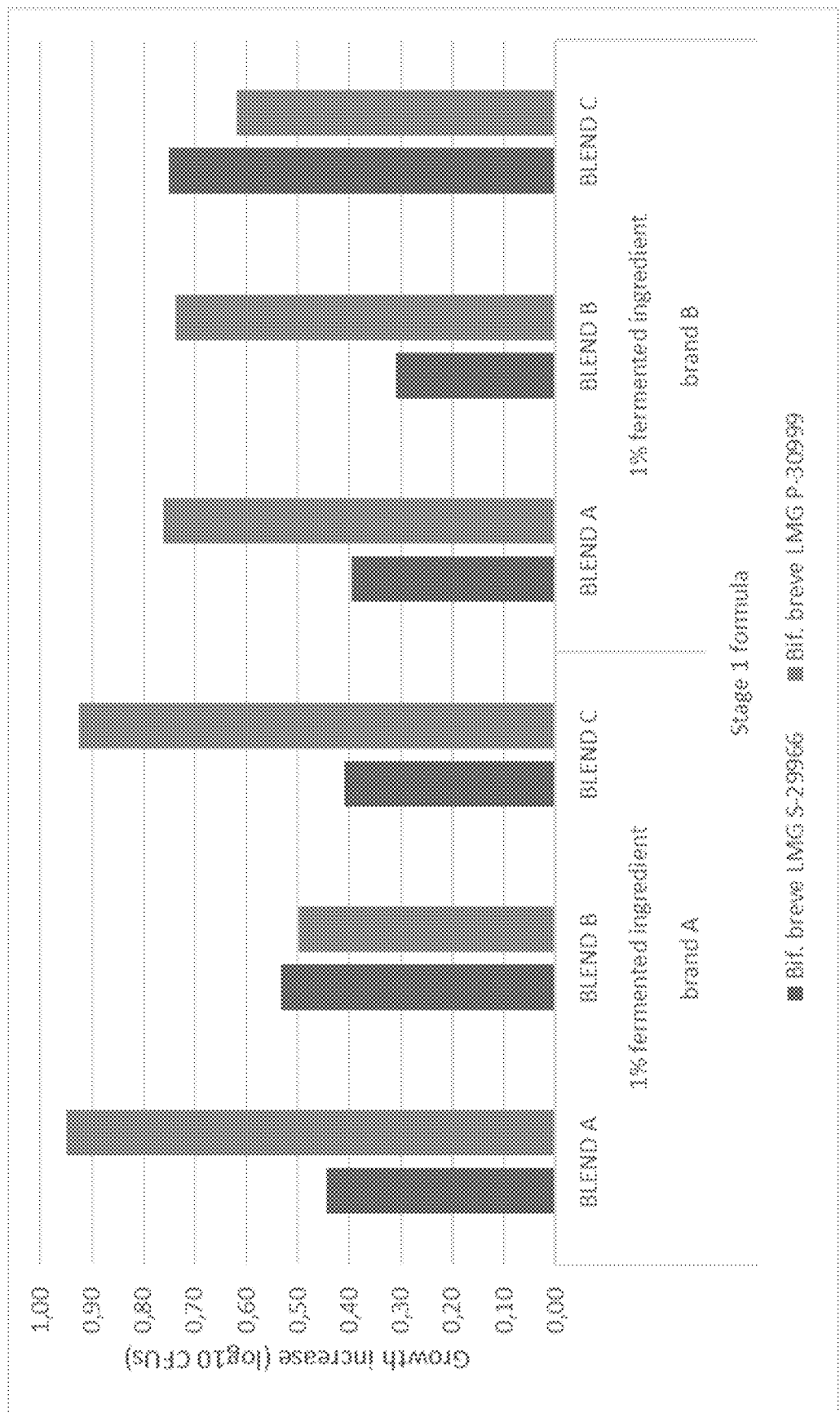

PRODUCTION METHOD TO INCREASE BIOAVAILABILITY OF SUGARS FROM NATURAL COMPLEX POLYSACCHARIDES FOR HUMAN, ANIMAL AND AGRICULTURAL PURPOSES

This application is a national stage application of PCT/EP2020/059126 filed on Mar. 31, 2020, which claims priorities of European patent application number 19167044.7 filed on Apr. 3, 2019. The disclosure of each of the foregoing applications is incorporated herein by reference in its entirety.

The present invention refers to fermented food products or food supplements and to a process for their preparation.

BACKGROUND OF THE INVENTION

Fermented foods are traditionally used for human nutrition from centuries, all over the world. Different types of foods are used as substrate for the fermentation process, including vegetables, meat, milk, fish, etc. The ecological environment strongly impacts the type of matrix to be fermented based on the prevalent availability of this substrate in that niche.

Fermentation is known to improve the nutritional value of the original substrate as well as to extend the so-called shelf-life of the food, allowing to store it for long time periods even in harsh environmental conditions.

Fermentation processes are based, especially for traditional food, on the activity of spontaneous communities of bacteria, fungi and yeast that, taken together, maximize their ability to take profit of the substrate. Some of the natural microbial fermenting communities represent wonderful examples of symbiosis between genetically different microbes. Unfortunately, natural spontaneous fermenting pools of microbes have to be preserved with continuity in order to maintain their features but the production of metabolites and flavors, associated to their fermentative activity, cannot be controlled. In most cases, this uncontrolled process is however not suitable for the industrial production of fermented food due to regulatory and safety requirements.

Fermented foods represent historically a valuable resource for the livelihoods of rural communities as well as for traditional artisanal local productions. Besides being a tool for income generation in this small-medium scale economy, fermentation assures stronger safety requisites and allows to design a very diversified pattern of processed foods suitable for long term storage, despite seasonal variations of natural resources. (FAO, 2012).

Usually fermented foods come from natural and spontaneous processes of degradation of food by natural communities of bacteria, yeast, fungi and molds that act together in order to take full metabolic advantage from the substrate. Traditional production processes by spontaneous fermenting communities are usually passed down by cultural and traditional values to subsequent generations.

Great diffusion of fermented food based on grain, fruit and vegetables as well as fermented alcoholic beverages demonstrate the relevance of fermented food in human nutrition. A detailed and comprehensive overview of the most known fermented food in the world was provided by FAO from 1998 to 2000.

The main reason for promoting fermented food is due to the acidification of the substrate that assures the prolongation of its shelf-life but other benefits are usually associated to this conventional technological advantage, that promoted at the very early beginning the development of fermented food in rural communities. Besides the preservative action of fermentation, it also provides palatability to nutritional substrates as well as improves their nutritional value e.g. by reducing the concentration in antinutrients. (Selhub et al. 2014).

Beneficial health effects are also traditionally attributed to fermented foods through the interaction of food with human gut microbiota and the positive impact that the improvement of the intestinal functions can have on the wellbeing of consumers. However, the mechanisms underlying these beneficial effects have not been clarified yet.

Naturally fermenting microbial communities are composed of complex groups of bacteria, fungi, mold, and yeast, some culturable and some non-culturable, able to utilize different food substrates (Tamang et al. 2016). Numerous research projects were focused on the comprehension of the composition of these natural spontaneous communities, that vary greatly in relation to various foods and beverages across the world. Anyway, the reliable identification of the different components based on taxonomic criteria is always a very difficult issue leading to an incomplete knowledge of these ecological groups.

Properly controlled fermentation can assure the maximization of beneficial nutrient and the reduction of potential deleterious effect due to antinutrients and contaminants, amplifying the beneficial action of fermented foods apart from their nutritive supporting action.

Current approach to the selection of starter strains for controlled fermentation of food is focused on the achievement of the best fermentative performances (e.g. yeast for fermenting flour for bakery) and/or to the reduction of risk of contamination (e.g. starter lactic acid bacteria for meat) and/or the promotion of the development of special and typical flavors and metabolites (e.g. starter strains for yoghurt, wine, etc).

On the other hand, probiotics are living microorganisms that, when administered in adequate amount, are able to exert beneficial effect on the host (FAO, 2002). Microbial strains with proven beneficial properties are available for human consumption as food (e.g. fermented milk) as well as food supplements and even drugs. The main and necessary feature to exert their beneficial action is that they have to be consumed in viable form and maintain their viability through the passage in the gut. Anyway, the use of probiotics in some critical conditions appears to be questionable in expert's opinion.

Carefully selected probiotics can be associated to different food substrates, other than milk, by performing a controlled fermentation able to maximize the properties of the substrate in terms of beneficial effect for special categories of population. Pregnant women, lactating mothers, baby during the weaning period usually suffer from an endogenous lack of bifidobacteria, a key group of bacteria whose beneficial functions mainly rely on the production of short chain fatty acids essential for the colonic functions. In order to promote the selective development of bifidobacteria, some prebiotics, such as fructo- and galacto-oligosaccharides are exogenously added to weaning foods (Sholtens et al. 2006).

Selected starter strains are developed at the industrial level in order to promote controlled fermentation of food. However, starter strains are usually selected for their technological features e.g. for their ability to rapidly degrade the substrate, but not for their potential benefit to the consumer and/or for their ability to improve the nutritional value of the food.

DESCRIPTION OF THE INVENTION

It has now been found that, by a suitable selection of a specific bacterial blend and of specific fermentation conditions, it is possible to obtain a new fermented ingredient for food and food supplements providing a beneficial action on the host, through the accumulation of useful metabolites from microbial activity as well as the reduction of antinutrients present in the original food substrate, such as phytates in cereals and legumes.

In particular, it has been found a specifically selected bacterial blend, composed of *Lactobacillus* gasseri, *Lactobacillus rhamnosus* and *Bifidobacterium breve* able to effectively ferment food of vegetable origin.

A first object of the invention accordingly comprises a fermented food product or food supplement comprising a vegetable substrate fermented by a probiotic blend consisting of *Lactobacillus* gasseri, *Lactobacillus rhamnosus* and *Bifidobacterium breve*.

A second object of the invention comprises a process for the preparation of a fermented food product or food supplement comprising a first fermentation step of a vegetal substrate with *L. rhamnosus* followed by a second fermentation step with *L. gasseri* and *Bifidobacterium breve*.

The invention also concerns the use of the obtained fermented food product or food supplement for improving natural maternity, lactation and baby weaning.

DETAILED DESCRIPTION OF THE INVENTION

Any strain of *L. gasseri, L. rhamnosus* and *Bifidobacterium breve* may be used according to the invention, in any ratio. A ratio of 1:1:1 expressed as cell count is preferred.

Preferred strains have been deposited at the BCCM/LMG collection at Ghent University (Belgium) under the Budapest treaty, under the following accession numbers:

*Lactobacillus* gasseri LMG P-30998
*Lactobacillus rhamnosus* LMG P-31000
*Bifidobacterium breve* LMG P-30999

The vegetable substrate which is subjected to fermentation by the probiotic blend according to the invention may be selected from oat, barley, corn, cereals, pseudo-cereals, gluten-free vegetables, vegetables, fruits, nuts, optionally in combination with an oil such as corn oil, sunflower oil, olive oil or the like. Oat is particularly preferred as a substrate, alone or in combination with corn oil, sunflower oil or other vegetal oils.

If desired, the fermented food product or food supplement of the invention may also contain an animal milk, preferably donkey or sheep milk.

The fermented food product of the invention may be in any form suitable for administration, e.g. in liquid, powder or cream form. Said food product may be used as food ingredient and/or food supplement, added in concentration ranging from 0.5 to 20% by weight to conventional food such as yogurt, milk, formula, fruit juices, soft-drinks, baby foods, fruit jams, and the like.

The probiotic blend used in the fermentation of the vegetable substrate is not viable in the food or food supplement of the invention which is submitted to a pasteurization process that assures that at the end of the production process it does not contain viable microbial cells. Depending on the final processing conditions the resulting ingredient has different composition and features depending on the inactivation and/or preservation of some microbial metabolites and catabolic/anabolic products.

The fermented food product or food supplement of the invention is prepared by a process comprising a first fermentation step of the vegetal substrate with *L. rhamnosus* followed by a second fermentation step with *L. gasseri* and *Bifidobacterium breve*. In fact, due to the inability of bifidobacteria to use oat drink as growth medium, and the only partial performances observed for *L. gasseri*, the fermentation is carried out by inoculating the medium with *L. rhamnosus* first and then, after correcting pH to 6.0, by adding *L. gasseri* and Bif breve. By this strategy (2-steps fermentation) the substrate is firstly degraded by *L. rhamnosus*, producing short chain sugars and free peptides and amino acids able to better support the growth of bifidobacteria.

As soon as the fermentation is complete, the substrate is subjected to thermal treatment to inactivate bacteria. The inactivated fermentation product can be directly used for animal or human consumption. Otherwise, the product is powdered by different technological approaches, e.g. by lyophilization, spray-drying or similar techniques.

In case of lyophilization, the inactivated fermented substrate is frozen to $-20°$ C.--$80°$ C. and then dried in a lyophilizer. Timing and drying conditions depends on the size of the apparatus. Final powder has a humidity content between 3.0 and 4.5%. A fine powder, white and with sweet taste is obtained. The % of recovery of the powder from the liquid fermented substrate is between 10 and 30%.

In case of spray-drying, the inactivated fermented substrate is directly fed to a spray drier and treated at different inlet and outlet temperatures (from 80 to $180°$ C.) and different fluxes (in ml per min). Final powder has a humidity content between 2.0 and 4.0%. The appearance of the powder is fine, from white to yellowish with sweet taste. The % of recovery of the powder from the liquid fermented substrate is between 20 and 60%. The assays conducted in order to set the optimal production conditions suggested that the low temperature of spraying gave higher % of recovery of the dried powder.

The two-step fermentation process allows to maximize the ability of the selected blend to improve the quality of the original food substrate by accumulating useful metabolites, by reducing the concentration of potentially dangerous substances and by increasing the digestibility of natural foods, particularly of vegetables.

The fermented food product of the invention provides a number of beneficial effects, including the stimulation of bifidobacteria, the decrease of anti-nutrients such as phytates, the improvement of natural maternity, lactation and baby weaning, the modulation of abdominal pain by acting on the endo-cannabinoid system of human gut mucosa, the promotion of the digestibility of natural vegetable food and increase in the bioavailability of some nutrients. By promoting the growth of bifidobacteria, improving thereby the composition of gut microbiota, the fermented food of the invention effectively antagonizes pathogenic bacteria or potentially harmful microbes. The invention accordingly enriches and improves the diet of special category of consumers with very restricted food choice, such as weaning babies and elderly people.

The efficacy of the new fermented food for the natural improvement of maternity, lactation and weaning was evaluated by means of several in-vitro tests finalized to measure the bifidogenic power (ability to act as a prebiotic substance, determining an increase of bifidobacteria) by direct inoculation of milk and by fecal fermentation model (FMF), to modulate abdominal pain by acting on the endo-cannabinoid system of human gut mucosa and to reduce the amount of antinutrients contained in natural matrices of vegetable origin, promoting the digestibility of natural vegetable food and increasing the bioavailability of nutrients. The obtained results are reported in the following examples.

Example 1—Preparation of the Fermented Food

The following blends of different strains obtained have been used and compared either according to the process of the invention, by performing first the fermentation with *L. rhamnosus* and then with the two other species, as reported above (two step fermentation), or by fermenting the substrate with the three species contemporaneously, in the same conditions reported for fermentation 1.

Blend A
  *Lactobacillus gasseri* L6
  *Lactobacillus rhamnosus* L13b
  *Bifidobacterium breve* 2TA Blend B
  *Lactobacillus gasseri* 20243
  *Lactobacillus rhamnosus* GG
  *Bifidobacterium breve* BB03

Blend C
  *Lactobacillus gasseri* LG36
  *Lactobacillus rhamnosus* Sp1
  *Bifidobacterium breve* M16V Preparation of mother cultures: preparation of washed pure cultures of the 3 strains composing the blend by culturing the three bacterial species in the culture medium, centrifugation to eliminate spent supernatant, washing with pure water and resuspension with fresh medium or pure water. Mother cultures are counted on plate to check viability.

Fermentation No. 1 (one-step fermentation): inoculation of the food substrate with 1% final concentration of *L. rhamnosus*, *L. gasseri* and Bif breve washed cultures ($10^\wedge$-$10^\wedge$ CFU/ml of medium).

Incubation for 18-24 hours at 37° C. in microaerophilic conditions, static or under slow agitation.

Final count of viable *L. rhamnosus*, *L. gasseri* and Bif breve at least $3\times10^\wedge8$ CFU/ml each, pH between 3 and 4.

Inactivation of viable cells of bacteria by thermal treatment e.g. pasteurisation at 65° C.×30 min.

Correction of the pH to 6.0-7.0 by sodium hydroxide (sodium bicarbonate and/or other alkaline reagents are also suitable).

Fermentation No. 2 (Two-Step Fermentation)

Phase 1—inoculation of the food substrate with 1% final concentration of *L. rhamnosus*, washed culture ($10^\wedge5$-$10^\wedge8$ CFU/ml of medium).

Incubation for 18-24 hours at 37° C. in microaerophilic conditions, static or under slow agitation.

Final count of viable *L. rhamnosus* at least $3\times10^\wedge8$ CFU/ml each, pH between 3 and 4.

Inactivation of viable cells of bacteria by thermal treatment e.g. pasteurisation at 65° C.×30 min.

Correction of the pH to 6.0-7.0 by sodium hydroxide (sodium bicarbonate and/or other alkaline reagents are also suitable).

Phase 2—Inoculation of the substrate fermented in Phase 1 with 1% final concentration of *L. gasseri* and Bif breve washed cultures ($10^\wedge5$-$10^\wedge8$ CFU/ml of medium).

Incubation for 18-24 hours at 37° C. in microaerophilic conditions, static or under slow agitation.

Final count of viable *L. gasseri* and Bif breve at least $3\times10^\wedge8$ CFU/ml each, pH between 3 and 4.

Inactivation of viable cells of bacteria by thermal treatment e.g. pasteurisation at 65° C.×30 min.

Correction of the pH to 6.0-7.0 by sodium hydroxide (sodium bicarbonate and/or other alkaline reagents are also suitable).

The final concentrations in viable cells and the growth gain obtained with the species indicated in the blends A, B and C above in the one- or two-steps fermentations are reported in Table 1.

TABLE 1

Comparison of the growth of the different blends (composed of three bacterial species) composing the blend in one-step fermentation process VERSUS two-step fermentation process. Total count of viable bacteria was performed at the end of the fermentation for both tested process, one-step, based on the simultaneous inoculum of the three bacterial species in the food substrate, and the two-step, based on a first fermentation with the species *L. rhamnosus* and, following complete inactivation of this species, by the fermentation with *L. gasseri* and *Bif. Breve*.

| Blend | Final concentration in viable cells (CFU/ml) | | Growth gain |
|---|---|---|---|
| | one-step ferm | two-step ferm | (log10 CFUs) |
| BLEND A | 8.72 | 8.88 | 0.16 |
| BLEND B | 8.65 | 9.11 | 0.46 |
| BLEND C | 8.46 | 9.24 | 0.77 |

The results reported in Table 1 show that the two-step fermentation secured an overall better performance of the blend and an increase in the final content in viable cells. Even if the obtained fermented food does not contain viable cells but only metabolic products from microbial fermentation, the concentration in viable microbial cells at the end of the fermentation process assures the final quality expected for the fermented food of the invention. It is evident that different strains provide, based on the same composition of the blend in terms of species, different results but all of them are able to assure, in a two-step fermentation process better results than in one-step fermentation.

The final concentrations of the single bacterial species composing the blends measured by selective counting of viable cells on laboratory growth media are reported in Table 2. Again, the two-step fermentation assures an improved growth of Bif breve and of *L. gasseri* (from 3.32 log 10 CFUs and 0.7 log 10 CFUs, respectively) compared to one-step process in which the three species are added simultaneously to the substrate.

TABLE 2

Comparison of the growth (as average of 3 different experiments) of the three bacterial species composing the blend in one-step fermentation process VERSUS two-step fermentation process.

| Strain | Final concentration in viable cells (log10 CFUs) | |
|---|---|---|
| | one-step ferm. | two-step ferm. |
| *B. breve* | 5.00 | 8.32 |
| *L. rhamnosus* | 8.23 | 8.86 |
| *L. gasseri* | 7.81 | 8.51 |

Example 2—Evaluation of the Bifidogenic Potential (Growth Assays in Milk)

The bifidogenic activity, i.e., the property to selectively support the growth of bifidobacterial. A bacterial genus naturally present in human gut producing beneficial metabolites such as short chain fatty acids, essential for the survival of colonocytes, was tested by adding fermented powders obtained as in Example 1 to commercial milk formulas (Chinese and Korean Ofmom® liquid formula). The modified milk was then inoculated with washed cultures of 5 reference bifidobacteria (strains Bif. breve LMG P-30999 and Bif. breve LMG S-29966) and their growth was checked and recorded in 24 hours. Results of modified milk were compared with the results previously achieved with the same normal milk formulas. Tests were performed on Stage 1 formula milk.

of main bacterial groups was monitored by quantitative PCR, comparing their concentration at time zero and following incubation in the presence of the fermented powder. Fluctuations in main bacterial groups were therefore evaluated to estimate the potential beneficial and/or detrimental effect of the new ingredient on human gut microbiota.

The ratio Firmicutes/Bacteroidetes (F/B) represents the first line of evaluation of the effect of the ingredient on human gut microbiota. Alterations of this ratio are associated to severe dysbiotic conditions such as those associated

TABLE 3

Growth of *bifidobacteria* (reference strains *Bif. breve* LMG S-29966 and *Bif. breve* LMG P-30999) in formula milk stage 1 (for 0-6 months babies) added with 1% final concentration of powdered fermented ingredient.

| | Stage 1 formula | | | | | | |
|---|---|---|---|---|---|---|---|
| | | brand A | | | | brand B | |
| Reference | Normal | 1% fermented ingredient | | original | 1% fermented ingredient | | |
| bifidobacteria | formula | BLEND A | BLEND B | BLEND C | recipe | BLEND A | BLEND B | BLEND C |
| *Bif. breve* LMG S-29966 | 7.64E+07 | 2.12E+08 | 2.61E+08 | 1.96E+08 | 4.73E+07 | 1.18E+08 | 9.64E+07 | 2.66E+08 |
| *Bif. breve* LMG P-30999 | 4.09E+07 | 3.64E+08 | 1.29E+08 | 3.45E+08 | 2.55E+07 | 1.47E+08 | 1.39E+08 | 1.06E+08 |

FIG. 1 shows the growth of bifidobacteria in stage-1 liquid formula milks added with 1% fermented ingredient of the invention, expressed as log 10 CFUs, normalized as difference between the growth of the microbial blend in formula added with the new ingredient versus the commercial formula.

The presence of the fermented ingredient allows bifidobacteria to growth better in milk in comparison to formula milk as acquired from the market (basic recipe). FIG. 1 shows that, independently from the commercial brand considered, bifidobacteria grow better in the presence of the fermented ingredient. Growth gain was in the range between 0.31 and 0.95 log 10 CFUs, depending on the blend used for the fermentation. The ability of the fermented ingredient to support the growth of bifidobacteria (bifidogenic power) was therefore confirmed in all of the tested experimental conditions.

Example 3—Evaluation of the Bifidogenic Potential by Fecal Fermentation Model (FMF)

Fermented powders of the invention were also checked for their bifidogenic power by means of FMF fecal fermentation. A laboratory model of gut fermentation was adopted to study how the ingestion of the fermented oat ingredient could impact the composition of gut microbiota by promoting beneficial bacteria so as to antagonize pathogenic bacteria or potentially harmful microbes.

The ingredient obtained as in Example 1 was added at 1% final conc. to a standardized pooled fecal sample in the presence of fresh growth medium, simulating the food assumed by the consumer. After incubation in appropriate conditions (anaerobiosis at 37° C. for 24 hours, the growth with obesity, gut chronic diseases, etc. Normal values are around 10, while significant altered ratios (e.g., values higher than 100) indicate an abnormal prevalence of Firmicutes, frequently associated to some diseases.

The fermented food of Example 1 was checked in FMF model in order to exclude its influence on the F/B ratio. The safety of the ingredient was confirmed also by the fact that the F/B ratio was not altered in the course of the assay, independently from the composition of the blends used for the fermentation of the natural substrate. Firmicutes were quantified in 8.0 log 10 CFUs in feces of healthy human donors at the beginning of the assay and 7.6 after assay in the presence of glucose. The presence of the fermented ingredient as carbon source lead to a range of values 7.4-7.7 log 10 CFUs. Bacteroidetes were found to be present at time zero in 7.8 log 10 CFUs. Following the completion of the assay, Bacteroidetes were 6.5 log 10 in the presence of glucose and in a range between 6.4-6.8 log 10 in the presence of the fermented ingredient.

F/B ratio was therefore calculated to be 1.03 in average at the beginning of the assay, increasing to 1.16 following incubation with glucose. The presence of the fermented ingredient lead to values 1.11-1.17. the ratio was confirmed not to be altered by the presence of the fermented ingredient.

The effect of the fermented ingredient on total bacteria was also assessed in order to exclude potential detrimental effect generated on bacterial groups other than bifidobacteria. A slight increase in total bacteria was observed, as expected in the presence of glucose with 0.3 log 10 increase in total bacteria. The fermented ingredient determines 0.3-0.4 log 10 increase in the growth of total bacteria, similarly to what was determined by glucose (reference carbon source).

The bifidogenic effect of the new fermented ingredient was confirmed by direct quantification of bifidobacteria in FMF model, as described above. Data of quantification of bifidobacteria by quantitative real-time PCR are provided in Table 4.

TABLE 4

Quantification of bifidobacteria in FMF model by comparing glucose as conventional carbon source and the new fermented ingredient. Time zero concentration was also measured as well as value obtained in the presence of non-fermented natural ingredient.

| Carbon source | Average copies number | FD | Count per gr of FMF | log | Growth gain (log10) |
|---|---|---|---|---|---|
| Glucose | 5.05E+06 | 46.9 | 4.74E+08 | 8.7 | 1.1 |
| NF powder | 1.67E+06 | 46.8 | 1.57E+08 | 8.2 | 0.6 |
| Blend A | 2.48E+06 | 44.5 | 2.21E+08 | 8.3 | 0.7 |
| Blend B | 3.40E+06 | 46.5 | 3.17E+08 | 8.5 | 0.9 |
| Blend C | 3.91E+06 | 57 | 4.45E+08 | 8.6 | 1.0 |
| Blend D | 3.55E+06 | 61.4 | 4.36E+08 | 8.6 | 1.0 |
| T0 | 3.66E+05 | 53 | 3.88E+07 | 7.6 | \ |

Bifidobacteria are stimulated to a significant extent following exposition to the fermented ingredient. Similar results of growth gain just slightly lower than glucose were obtained.

The effect of the fermented ingredient was also checked on a large range of final concentrations in order to demonstrate that its efficacy is dose-dependent and in which manner this association is expressed.

TABLE 5

Quantification of bifidobacteria in FMF model by comparing different final concentrations of the fermented ingredient. Glucose was checked as positive control as conventional carbon source. Time zero level of bifidobacteria was also measured as well as the value obtained in the presence of non-fermented ingredient (used as negative control).

| | CFU/ml | Log10 | Growth gain (log10) |
|---|---|---|---|
| T0 | 4.20E+07 | 7.6 | \ |
| T48 NF powder | 5.90E+07 | 7.8 | \ |
| T48 glucose | 1.30E+09 | 9.1 | 1.3 |
| T48 0.5% ingr | 8.70E+08 | 8.9 | 1.2 |
| T48 1% ingr | 1.00E+09 | 9 | 1.2 |
| T48 1.5% ingr | 1.30E+09 | 9.1 | 1.3 |
| T48 2% ingr | 1.50E+09 | 9.2 | 1.4 |
| T48 3% ingr | 2.10E+09 | 9.3 | 1.5 |
| T48 5% ingr | 1.60E+09 | 9.2 | 1.4 |

The stimulation of bifidobacteria by the fermented ingredient was confirmed in a range of final concentration from 0.5 to 5%. The best result in terms of activation of bifidobacteria was achieved by the final concentration of 3% that can be considered as the best dose to be assumed daily by consumers to induce positive bifidogenic effect.

Example 4—Improved Digestibility Compared to the Same Natural Non-Fermented Substrate The content in antinutrients of the food ingredient of the invention was evaluated. Phytic acid is the primary source of inositol and storage phosphorus in plant seeds contributing at 70% of total phosphorus. The abundance of phytic acid in cereal grains and food of vegetable origin is a concern in the food and animal feed industries because the phosphorus in this form is unavailable to monogastric animals due to a lack of endogenous phytases, enzymes specific for the dephosphorylation of phytic acid. In addition, the strong chelating characteristic of phytic acid reduces the bioavailability of other essential dietary nutrients such as minerals, e.g. $Ca^{2+}$, $Zn^{2+}$, $Mg^{2+}$, $Mn^{2+}$, $Fe^{2+/3+}$, proteins and amino acids. The assay was conducted by the Megazyme® kit for the determination of phytate compounds.

Levels of antinutrients of food matrices, like phytates, decrease after the fermentation by the selected blend, as shown in Table 6. Different vegetable substrates were compared, by comparing non-fermented substrate with the fermented food according to the invention. The lowest concentration of phytate was detected in fermented ingredients oat-based, with values of 1.34 and 1.17 g per 100 g of fermented ingredient. Also in the rice, the levels of phytate decrease following fermentation according to the invention.

TABLE 6

Decrease in the final concentration of phytates in fermented ingredient compared to the non-fermented natural substrate, with reference to different type of vegetables.

| Substrate | Phytate (g/100 g) |
|---|---|
| Non-fermented oat | 2.98 |
| Fermented oat blend A | 1.34 |
| Fermented oat blend B | 1.17 |
| Fermented oat blend C | 1.44 |
| Fermented oat blend D | 1.71 |
| Non-fermented rice | 1.79 |
| Fermented rice blend A | 0.86 |
| Fermented rice blend B | 0.02 |
| Fermented rice blend C | 0.70 |
| Fermented rice blend D | 1.10 |
| Non-fermented carrot | 0.02 |
| Fermented carrot blend A | 0.01 |
| Fermented carrot blend B | 0.00 |
| Fermented carrot blend C | 0.02 |

As expected, carrot was found to contain low level of phytates that almost disappeared following fermentation. Significant reduction was achieved in other substrates, such as cereals, naturally carrying a significant amount of phytates. Fermentation of the substrates with the selected blend led to the production of fermented powders naturally lowered in these antinutrient compounds. Lowering was of significant entity since phytate were halved with some of the tested microbial blends.

Example 5 Comparative tests An oat aqueous substrate was fermented with an organism blend according to EP 1169925 and with an organism blend according to the invention.

The tests have been carried out either according to the method disclosed in US 2010098805 or according to the method of the invention Two Steps Fermentation According to US 2010098805

The aqueous substrate based on oat was incubated for 24 hours at 37° C. in order to let the naturally present microorganisms to develop inside the substrate. After incubation, the naturally fermented biomass is pasteurized in order to inactivate viable bacteria. The resulting product form first fermentation was then inoculated with strains *L. casei* ATCC334, *L. acidophilus* ATCC4356, *B. breve* ATCC15700 *B. longum* ATCC15707, *B. longum* sub. infantis ATCC15697 (Blend B) mixed together at the same time (second fermentation step). Viable counts on different selective media were performed to precisely quantified the inoculum size. MRS agar for the total *Lactobacillus* spp. viable counts. MRS supplemented with 10 mg/ml of vancomycin for the enumeration of *L. casei* ATCC334, and MRS supplemented with 0.1 and 10 μg/ml of clindamycin and ciprofloxacin for the enumeration of *L. acidophilus* ATCC4256. The TOS propionate agar base medium (Sigma-Aldrich Merck) supplemented with mupirocin 50 mg/i for the enumeration of *Bifidobacterium* genus.

The fermentation bulk was incubated for 24 h at 37° C. under microaerophilic conditions. Following incubation, viable counts were performed on the above-mentioned selective media to evaluate the final concentration reached by the microorganisms. The fermented biomass was then inactivated as previously described. The same procedure was repeated using in the second fermentation a blend consisting of Lactobacillus gasseri L6, Lactobacillus rhamnosus L13b and Bifidobacterium breve 2TA (Blend A).

Two Steps Fermentation According to the Invention

The process of example 1 has been repeated using blend A. Blend B was also subjected to a similar process, using L. paracasei ATCC334 in the first fermentation step in substitution of L. rhamnosus. L. paracasei has in fact the closest phylogenetical similarity to L. rhamnosus.

RESULTS

The growth (in log 10 CFUs) of the two blends by the methods of the invention and of US 2010098805 s reported in Table 7. The data have been obtained by decimal count difference in plate between the growth time T24 and time T0 (start of fermentation) for each strain under examination. The three bifidobacteria strains of blend B have been measured by means of quantitative PCR.

| Strains/blend | Method of US201098805 | | Method of the invention | |
| --- | --- | --- | --- | --- |
| | Plate count | qPCR | Plate count | qPCR |
| Blend A | | | | |
| B. breve 2Ta | −0.09 | \ | 1.29 | \ |
| L. gasseri L6 | −0.04 | \ | 2.97 | \ |
| L. rhamnosus L13b | 2.89 | \ | 2.64 | \ |
| Blend B | | | | |
| L. paracasei ATCC 334 | 2.63 | \ | 2.88 | \ |
| L. acidophilus ATCC 4356 | −0.02 | \ | 3.03 | \ |
| B. breve ATCC 15700 | 0.47 | 0.13 | 2.03 | 0.60 |
| B. longum subs infantis ATCC 15697 | | 0.15 | | 0.67 |
| B. longum ATCC 15707 | | 0.19 | | 0.76 |

The data in Table 7 show that the fermentation method of US 2010098805 does not allow the growth of 2 out of 3 strains of blend A.

On the contrary, the two steps fermentation method of the invention enables the growth of the three strains of blend A as well as of the strains of blend B disclosed in EP 1169925 to the same extent to that of blend A for the species L. rhamnosus (phylogenetically similar to L. paracasei) and L. gasseri (phylogenetically similar to L. acidophilus).

In addition, the method of the invention enables a more efficient fermentation of Bif breve in comparison to the other bifidobacteria included in blend B.

Blend B could not replicate the performances of blend A, when subjected to the same fermentation methods and conditions.

REFERENCES

1. Lichtenberger, L. M. THE HYDROPHOBIC BARRIER PROPERTIES OF GASTROINTESTINAL MUCUS. Annu. Rev. Physioi (1995). doi:10.1146/annurev-.physiol.57.1.565
2. Duary, R. K., Rajput, Y. S., Batish, V. K. & Grover, S. Assessing the adhesion of putative indigenous probiotic lactobacilli to human colonic epithelial cells. Indian J. Med. Res. (2011). doi:10.4103/0971-5916.90992
3. Deepika, G., Karunakaran, E., Hurley, C. R., Biggs, C. A. & Charalampopoulos, D.
   Influence of fermentation conditions on the surface properties and adhesion of Lactobacillus rhamnosus GG. Microb. Cell Fact. (2012). doi:10.1186/1475-2859-11-116
4. Rousseaux, C. et al. Lactobacillus acidophilus modulates intestinal pain and induces opioid and cannabinoid receptors. Nat. Med. 13, 35-37 (2007).
5. Wang, L. et al. Activation of epidermal growth factor receptor mediates mucin production stimulated by p40, a Lactobacillus rhamnosus GG-derived protein. J. Biol. Chem. (2014). doi:10.1074/jbc.M114.553800
6. Wong, B. S. et al. Pharmacogenetic trial of a cannabinoid agonist shows reduced fasting colonic motility in patients with nonconstipated irritable bowel syndrome. Gastroenterology (2011). doi:10.1053/j.gastro.2011.07.036
7. Hermanson, D. J. & Marnett, L. J. Cannabinoids, endocannabinoids, and cancer. Cancer Metastasis Rev. (2011). doi:10.1007/s10555-011-9318-8
8. Johansson, M. L. et al. Administration of different Lactobacillus strains in fermented oatmeal soup: In vivo colonization of human intestinal mucosa and effect on the indigenous flora. Appl. Environ. Microbiol. 59, 15-20 (1993).
9. El-Abasy, A. E., Abou-Gharbia, A., H., Mousa, H. M. & Youssef, M. M. Mixes of Carrot Juice and Some Fermented Dairy Products: Potentiality as Novel Functional Beverages. Food Nutr. Sci. (2012). doi:10.4236/fns.2012.32034
10. Daneluti, A. L. M. & Matos, J. do R. Study of thermal behavior of phytic acid. Brazilian J. Pharm. Sci. (2013). doi:10.1590/S1984-82502013000200009
11. Marshall E. & Mejia D. (2012) Traditional fermented food and beverages FAO Diversification booklet n. 21.
12. FAO. 2000a. Fermented Grain Legumes, Seeds and Nuts: A Global Perspective, FAO Agricultural Services Bulletin No. 142, Rome.
13. FAO.2000b. Grain legumes, seeds and nuts: rationale for fermentation. Fermented Grain Legumes, Seeds and Nuts: A Global Perspective, FAO Agricultural Services Bulletin No 142, Rome.
14. FAO. 1999. Fermented Cereals—A Global Perspective, FAO Agricultural Services Bulletin No 138, Rome.
15. FAO. 1998. Fermented Fruits and Vegetables—A Global Perspective, FAO Agricultural Services Bulletin No. 134, Rome.
16. Selhub E M, Logan A C, Bested A C. Fermented foods, microbiota, and mental health: ancient practice meets nutritional psychiatry. J Physiol Anthropol. 2014; 33(1):2. Published 2014 Jan. 15. doi:10.1186/1880-6805-33-2
17. Tamang J P, Watanabe K, Holzapfel W H. Review: Diversity of Microorganisms in Global Fermented Foods and Beverages. Front Microbiol. 2016; 7:377. Published 2016 March 24. doi:10.3389/fmicb.2016.00377
18. Joint FAO/WHO Working Group Report on Drafting Guidelines for the Evaluation of Probiotics in Food London, Ontario, Canada, April 30 and May 1, 2002
19. Scholtens, Petra A. M. J., Alles, Martine S., Bindels, Jacques G., van der Linde, Esmeralda G. M., Tolboom, Jules J. M., Knol, Jan. Journal of Pediatric Gastroenterology and Nutrition: May 2006—Volume 42—Issue 5—p 553-559 doi: 10.1097/01.mpg.0000221887.28877.c7

The invention claimed is:

1. A fermented product obtained by:
generating short chain sugars, free peptides and amino acids by performing a first fermentation, by inoculating a plant substrate with *Lactobacillus rhamnosus* LMG P-31000;
adjusting pH of the plant substrate to 6.0 to 7.0; and
performing a second fermentation by inoculating the plant substrate with a probiotic blend comprising *Lactobacillus gasseri* LMG P-30998 and *Bifidobacterium breve* LMG P-30999.

2. The fermented product according to claim 1, wherein the plant substrate includes vegetables and at least one of a fruit, a nut, a grain, a cereal, and a pseudo-cereal.

3. The fermented product according to claim 1, wherein the plant substrate is oat.

4. The fermented product according to claim 1, wherein the plant substrate is oat in combination with an oil selected from the group consisting of: corn oil, sunflower oil, and olive oil.

5. The fermented product according to claim 1, wherein a CFU ratio of said *L. rhamnosus* inoculated in the first fermentation, said *L. gasseri* inoculated in the second fermentation, and said *Bifidobacterium breve* inoculated in the second fermentation is 1:1:1.

6. The fermented product according to claim 1, wherein the probiotic blend further comprises *L. rhamnosus*.

7. The fermented product according to claim 1, wherein the plant substrate is combined with donkey or sheep milk.

8. A method of manufacturing a fermented product comprising:
generating short chain sugars, free peptides and amino acids by performing a first fermentation by inoculating a plant substrate with *Lactobacillus rhamnosus* LMG P-31000;
adjusting pH of the plant substrate to 6.0 to 7.0; and
performing a second fermentation by inoculating the plant substrate with a probiotic blend comprising *Lactobacillus gasseri* LMG P-30998 and *Bifidobacterium breve* LMG P-30999.

9. The method of manufacturing the fermented product according to claim 8, further comprising spray-drying by feeding the fermented plant substrate to a spray drier,
wherein an inlet temperature and an outlet temperature of the spray drier are different.

10. A food item comprising the fermented product according to claim 1.

11. The food item according to claim 10 being in form of drink, cream, spread or powder.

* * * * *